United States Patent [19]
Walker et al.

[11] Patent Number: 5,976,871
[45] Date of Patent: Nov. 2, 1999

[54] CYTOGENETIC CHAMBER

[75] Inventors: Richard Walker, Hudsonville; Andrew Veldt, Kalamazoo; Kevin Ewing, Holland; Daniel Dorn, Thompsonville, all of Mich.; Jack L. Spurbeck, Kasson; Syed M. Jalal, Rochester, both of Minn.

[73] Assignee: Venturedyne, Ltd., Milwaukee, Wis.

[21] Appl. No.: 09/069,560

[22] Filed: Apr. 29, 1998

Related U.S. Application Data

[62] Division of application No. 08/886,981, Jul. 2, 1997, Pat. No. 5,851,790.

[51] Int. Cl.⁶ ........................................... C12M 1/02
[52] U.S. Cl. ................................. 435/307.1; 435/303.1; 435/809; 422/104; 312/1; 312/236
[58] Field of Search ............................ 435/286.6, 303.1, 435/307.1, 809; 422/104; 312/1, 236; 119/6.5, 6.6, 300; 600/21, 22

[56] References Cited

U.S. PATENT DOCUMENTS

| | | |
|---|---|---|
| 2,470,721 | 5/1949 | Pragel . |
| 2,695,605 | 11/1954 | Gibbon ........................................ 128/1 |
| 2,708,927 | 5/1955 | Dixon et al. . |

(List continued on next page.)

FOREIGN PATENT DOCUMENTS

| | | |
|---|---|---|
| 4-268435 | 9/1992 | Japan . |
| 1399681 | 5/1988 | Russian Federation ............... 435/40.5 |
| 2 215 260 | 9/1989 | United Kingdom ........................ 312/1 |

OTHER PUBLICATIONS

Box GEP, Hunter WG, Hunter JS (1978): "Statistics for Experimenters." New York: J. Wiley & Sons. pp. 510–539.
Hsu TC (1952): Mammalian chromosomes in vitro 1. The karyotype of man, Jour Hered 43:167–172.
Kalbfleisch JD, Printice RL (1980): "The Statistical Analysis of Failure Time Data." New York: J.Wiley & Sons, pp. 70–118.
Nowell PC (1960): Differentiation of human leukemic leukocytes in tissue culture. Exp Cell Res 19:267–277.
Moorhead PS, Nowell PC, Mellman WJ, Battips DM, Hungerford DA (1960): Chromosome preparations of leukocytes cultured from human peripheral blood. Exp Cell Res 20:613–616.
Nowell PC (1960): Phytohemagglutinin: an initiator of mitosis in cultures of normal human leukocytes. Cancer Res 20:462–466.
Peakman DC, Moreton MF, Corn BJ, Robinson A (1979): Chromosome mosaicism an amniotic fluid cell cultures. Am J Hum Genet 31:149–155.
Rothels KH, Siminovitch L (1958): An air drying technique for flattening chromosomes in mammalian cells grown in vito. Stain Technol 33:73–77.
Spurbeck JL (1991): Amniotic fluid harvest for high resolution: in situ using ethidium bromide. In Burch M (ed) "The ACT Cytogenetics Laboratory Manual," 2nd ed. Houston: Raven Press, pp. 96–97.

(List continued on next page.)

*Primary Examiner*—William H. Beisner
*Attorney, Agent, or Firm*—Jansson, Shupe, Bridge & Munger, Ltd.

[57] ABSTRACT

The cytogenetic chamber includes a chamber enclosure, a drying cavity in the enclosure, a door and a hand-insertion port through the door. A slide-supported, fixative-treated cell (prepared outside the chamber or in situ in the chamber) is in the drying area and air flows through the entirety of the drying area at a substantially uniform (and relatively low) flow rate. The fixative dries at substantially the same drying rate, irrespective of the location of the slide in the drying area. The invention is particularly useful for chromosome spreading and results in a significantly-increased percentage of metaphases having metaphase areas in the optimal range of 2,500 to 4,500 squared microns.

18 Claims, 6 Drawing Sheets

U.S. PATENT DOCUMENTS

| | | |
|---|---|---|
| 2,803,370 | 8/1957 | Lennard . |
| 3,117,009 | 1/1964 | Boelter ............................ 99/116 |
| 3,616,264 | 10/1971 | Ray et al. ....................... 195/127 |
| 3,618,734 | 11/1971 | Khan et al. ..................... 195/139 |
| 3,660,242 | 5/1972 | Gordon et al. .................. 195/139 |
| 3,701,201 | 10/1972 | Drury ................................. 34/60 |
| 3,825,723 | 7/1974 | Roeser ........................... 219/401 |
| 3,977,091 | 8/1976 | Hortig et al. ..................... 34/105 |
| 4,043,292 | 8/1977 | Rogers et al. ..................... 118/5 |
| 4,110,167 | 8/1978 | Melnyk ........................... 195/127 |
| 4,111,753 | 9/1978 | Folsom et al. ................... 195/126 |
| 4,179,984 | 12/1979 | Gorcey ....................... 98/115 LH |
| 4,236,063 | 11/1980 | Glucksman ..................... 219/400 |
| 4,286,456 | 9/1981 | Sisti et al. ........................ 73/23.1 |
| 4,331,254 | 5/1982 | Haggerty . |
| 4,356,967 | 11/1982 | Lunick ............................. 237/14 |
| 4,413,584 | 11/1983 | DiMaggio, Jr. et al. ........... 118/56 |
| 4,572,427 | 2/1986 | Selfridge et al. ..................... 236/3 |
| 4,689,303 | 8/1987 | Kraft et al. ..................... 435/290 |
| 4,696,902 | 9/1987 | Bisconte ........................ 435/300 |
| 4,701,415 | 10/1987 | Dutton et al. .................. 435/289 |
| 4,707,587 | 11/1987 | Greenblatt ..................... 219/299 |
| 4,892,830 | 1/1990 | Findley et al. .................. 435/284 |
| 4,923,816 | 5/1990 | Heeg et al. ..................... 435/284 |
| 5,178,094 | 1/1993 | Carr et al. . |
| 5,316,560 | 5/1994 | Drone-Schmidt et al. . |
| 5,410,985 | 5/1995 | Schritz ............................. 119/37 |
| 5,424,209 | 6/1995 | Kearney . |

OTHER PUBLICATIONS

Spurbeck JL, Carlson RO, Allen JE, Dewald GW (1988): Culturing and robotic harvesting of boen marrow, lumph nodes, peripheral blood, fibroblast and solid tumors with in situ tecniques. Cancer Genet Cytogenet 32:59–66.

Tjio JH, Levan A (1956) The chromosome number of man. Hereditas 42:1–6.

Yunis JJ (1976): High resolution of human chromosomes. Science 191:1268–127.

Medline Abstract #92373675 of Yamada et al. "Development of an Instrument for Chromosome Slide Preparation" Journal of Radiation Research (Mar. 1992); pp. 242–249.

English Translation of Miyasaka et al. JP 4–268435 (Dec. 1996).

Yamada et al. "Development of an Instrument for Chromosome Slide Preparation." J. Radiat Res. vol. 33 (1992) pp. 242–249.

FIG. 10

CYTOGENETIC CHAMBER

RELATED APPLICATION

This application is a division of application Ser. No. 08/886,981 filed on Jul. 2, 1997, and now U.S. Pat. No. 5,851,790.

FIELD OF THE INVENTION

This invention relates generally to cytogenetics and, more particularly, to preparing cells for microscopic analysis of chromosomes and possible defects therein.

BACKGROUND OF THE INVENTION

For some time, it has been known that cells, human cells, can be treated to "spread" the chromosomes so that they might be analyzed under a microscope for possible defects. The breakthroughs in cytogenetic techniques have been of landmark proportions in the last few decades. Examples include introduction of the hypotonic treatment in the 50s (HSu 1952), use of PHA to stimulate lymphocyte culture in the 60s (Nowell et al. 1960a; Nowell et al. 1960b), the ability to induce high resolution banding (Yunis et al. 1976) and development of in situ culture methods (Peakman et al. 1979; Spurbeck et al. 1988a) and robotic harvesting (Spurbeck et al. 1988b) during the 70s and 80s.

In spite of these remarkable advancements in cytogenetic techniques, consistency of optimum spreading of chromosomes remains a major problem. The consistency with which one could obtain optimum chromosome spreading of cytogenetic specimens has been a major concern.

From an examination of prior art, it is apparent that incubators used to grow cell cultures using live cells are unsuited for cytogenetic analysis. (It is understood that cell culturing is carried out in Petri dishes or other shallow vessels capable of holding a liquid such as a cell nutrient. The very name "incubator" implies sustenance of life.)

U.S. Pat. Nos. 4,572,427 (Selfridge et al.); 4,689,303 (Kraft et al.); 4,696,902 (Bisconte); 4,701,415 (Dutton et al.) and 4,923,816 (Heeg et al.) disclose and seem to typify such incubators. The incubators disclosed in such patents appear suitable for use by but one person at a time and require door opening to place the cell cultures.

The Selfridge et al. and Dutton et al. patents describe incubators said to be useful in growing cell cultures. Chamber atmosphere is controlled as to concentrations of one or more constituent gases (e.g., oxygen and carbon dioxide) and as to humidity.

The Kraft et al. patent discloses an incubator for treating cultures placed on microplates. Several microplates are placed on each of several vertically-spaced trays and each tray has an angularly-upturned lip which juts outward beyond the lip of the tray above it. Some of the air circulating past the lips is diverted by each lip and thereby directed across the surface of the microplates on that tray. In other words, the direction of air flow differs, depending upon what area of the incubator interior is being considered.

The Kraft et al. incubator has carbon dioxide and oxygen sensors and the patent mentions that temperatures in the range of 37° C. (99° F.) to 50° C. (122° F.) are used for incubation. Gas flow rates of 250 feet (760 cm.) per minute and 1000 feet (3050 cm.) per minute are also mentioned. The enclosure is of the double-door type.

The gassing incubator described in the Heeg et al. patent has two doors, both of which are transparent. Such patent implies that humidities of 90% and higher are used for cell culturing.

The Bisconte patent also describes an apparatus for cell culture. Cells to be cultured are in each of several storage devices within the enclosure, with each storage device holding multiple culture containers. Each container is in a respective sealed compartment and as a consequence, cells being cultured are shielded from direct air flow. Such shielding (and the use of high humidity as noted above) seemingly is to prevent drying of the culture. In its mention of how high air flow rates "tend to dry out biological culture media," the Dutton et al. patent appears to be in support of the idea that drying is undesirable when incubating cells.

Certainly, incubators are suitable for growing cell cultures but from the foregoing, it seems apparent that incubators are inappropriate for cell drying. A chamber configured for cytogenetic analysis and cell drying would be an important advance in the art.

OBJECTS OF THE INVENTION

It is an object of the invention to provide a chamber configured for cytogenetic analysis.

Another object of the invention is to provide a cytogenetic chamber for drying fixative-treated cells.

Another object of the invention is to provide a cytogenetic chamber which dries fixative-treated cells using very low air flow rates.

Another object of the invention is to provide a cytogenetic chamber permitting very precise control of temperature.

Another object of the invention is to provide a cytogenetic chamber permitting very precise control of relative humidity.

Still another object of the invention is to provide a cytogenetic chamber for use with cells prepared in situ or non in situ.

Another object of the invention is to provide a cytogenetic chamber which yields a comparatively-high percentage of optimum metaphase areas.

Yet another object of the invention is to provide a cytogenetic chamber which is optionally configured for use by two persons simultaneously.

Another object of the invention is to provide a cytogenetic chamber which includes an optional "baffle-like" valve for selecting air flow rate.

Another object of the invention is to provide a cytogenetic chamber which dries fixative-treated cells using air flowing in substantially a uniform direction. How these and other objects are accomplished will become apparent from the following descriptions and from the drawings.

SUMMARY OF THE INVENTION

The new cytogenetic chamber is particularly useful for drying fixative-treated metaphase and interphase cells (especially human cells) in a way that "fixes" the chromosomes in a spread-apart relationship. Such chromosomes may thereby be more readily analyzed by microscope to, for example, detect possible genetic defects.

(Parenthetically, the application of a fixative will also kill the cell—cytogenetic analysis is with respect to dead cells. As used in this specification, a fixative is any substance useful for the purposes described herein, e.g., fixing chromosomes in a spread-apart relationship.)

The new chamber has an enclosure, a drying cavity in the enclosure and a cavity access door mounted with respect to such enclosure. Such door is movable between open and closed positions and includes at least one (and preferably two) hand-insertion ports. A cell placed on a slide may be prepared in situ or non in situ and placed on a rack-like shelf in the cavity drying area for fixative drying. The chamber has an air-moving system which provides laminar air flow through the cavity and its drying area. In an optional arrangement, the chamber includes an adjustable bypass valve so that the volume of air flowing through the drying area per unit of time, i.e., flow rate, may be selected.

A highly-preferred chamber is configured so that both the temperature and the humidity of the air flowing through the drying area can be regulated within rather narrow limits. To that end, the chamber has a heater and, most preferably for humidity regulation as well as for controlling air temperature) a refrigeration system mounted with respect to the enclosure.

The chamber also has a steam generator and a condensing coil (an adjunct of the refrigeration system) for controlling the relative humidity (rh) of air in the drying cavity. The steam generator increases humidity and the condensing coil decreases humidity. (It is noted that while making the chamber more complex in construction and less precise in regulation, a dry air injector could be used for humidity regulation.)

It is advantageous to be able to prepare cells inside the chamber cavity and to maintain containers of liquids used in such preparation generally at the temperature of the air in the cavity. The new chamber also has a tray in the enclosure for holding such containers. The preferred chamber configuration permits reaching through a hand-insertion port, preparing a fixative-treated cell on a slide, placing the slide on a chamber rack and drying the fixative, all while retaining the door in the closed position. (It is to be appreciated that a fixative may be applied to a cell or a slide or cells may be in a closed container and "premixed" with a fixative.)

In another optional configuration, the chamber may be "double-sided." That is, the chamber may have two access doors, one each at the front and rear of the chamber. Each door has at least one hand-insertion port so that the chamber may be used simultaneously by two persons.

With a fixative-treated slide in the chamber drying area, air flows through the entirety of the drying area at a substantially uniform flow rate and in substantially the same direction. Preferably, the temperature of the air flowing through the drying area (and impinging on the fixative) is substantially uniform throughout such area and, most preferably, the relative humidity of the air flowing through the drying area is also substantially uniform throughout such area. The fixative dries at substantially the same drying rate, irrespective of the location of the slide in the drying area.

Preferred velocity of air flowing through the drying area is not in excess of about 50 feet (about 152 cm.) per minute and, most preferably, not in excess of about 25 feet (about 76 cm.) per minute. Preferred air temperature is between 15° C. (59° F.) and 40° C. (104° F.) and preferred relative humidity is between 25% and 75%.

(Optimum metaphase areas in the range of 2,100 to 4,500 squared microns—and, most preferably, in the range of 2,500 to 4,500 squared microns—can be achieved at various combinations of relative humidity and temperature. However, it has been found that for amniocytes, 55% rh at 20° C. (68° F.) and for lymphocytes 60% rh at 20° C. provides the best opportunity—30% or so—to obtain optimum metaphase areas.)

A new method for drying a fixative-treated cell supported on a slide includes the steps of providing a cytogenetic chamber with, optionally, a bypass valve which may be adjusted to select the volume of air flowing through the drying area per unit time. The chamber has an access door mounted for movement between closed and open positions.

While retaining the door in the closed position, a fixative is applied to the cell (or a fixative-cell mixture is placed on a slide), the slide is placed on a chamber shelf and the fixative is dried. The applying step includes extending a hand through a hand-insertion port prior to applying the fixative and, most advantageously (at least for convenience), the fixative container is available on the tray described above.

The placing step includes grasping the slide with the hand extended through the port and placing the slide at any location in the drying area. The drying step includes flowing air through the drying area at a substantially uniform flow rate and, preferably, in a substantially uniform direction.

In a specific configuration, the hand-insertion port includes two panels, each having a straight slit across it. With such configuration, the extending step includes extending the hand sequentially through the panel slits. (The term "slide" used in this specification means any type of transparent cell-supporting device, whether curved, flat or otherwise.)

Other details of the invention are set forth in the detailed description and in the drawings.

BRIEF DESCRIPTION OF THE DRAWINGS

FIG. 7 is a cutaway end elevation view of the chamber showing internal features. FIG. 7 is taken from the perspective of viewing axis VA5. Parts are broken away.

DETAILED DESCRIPTION OF PREFERRED EMBODIMENTS

Figure 1:
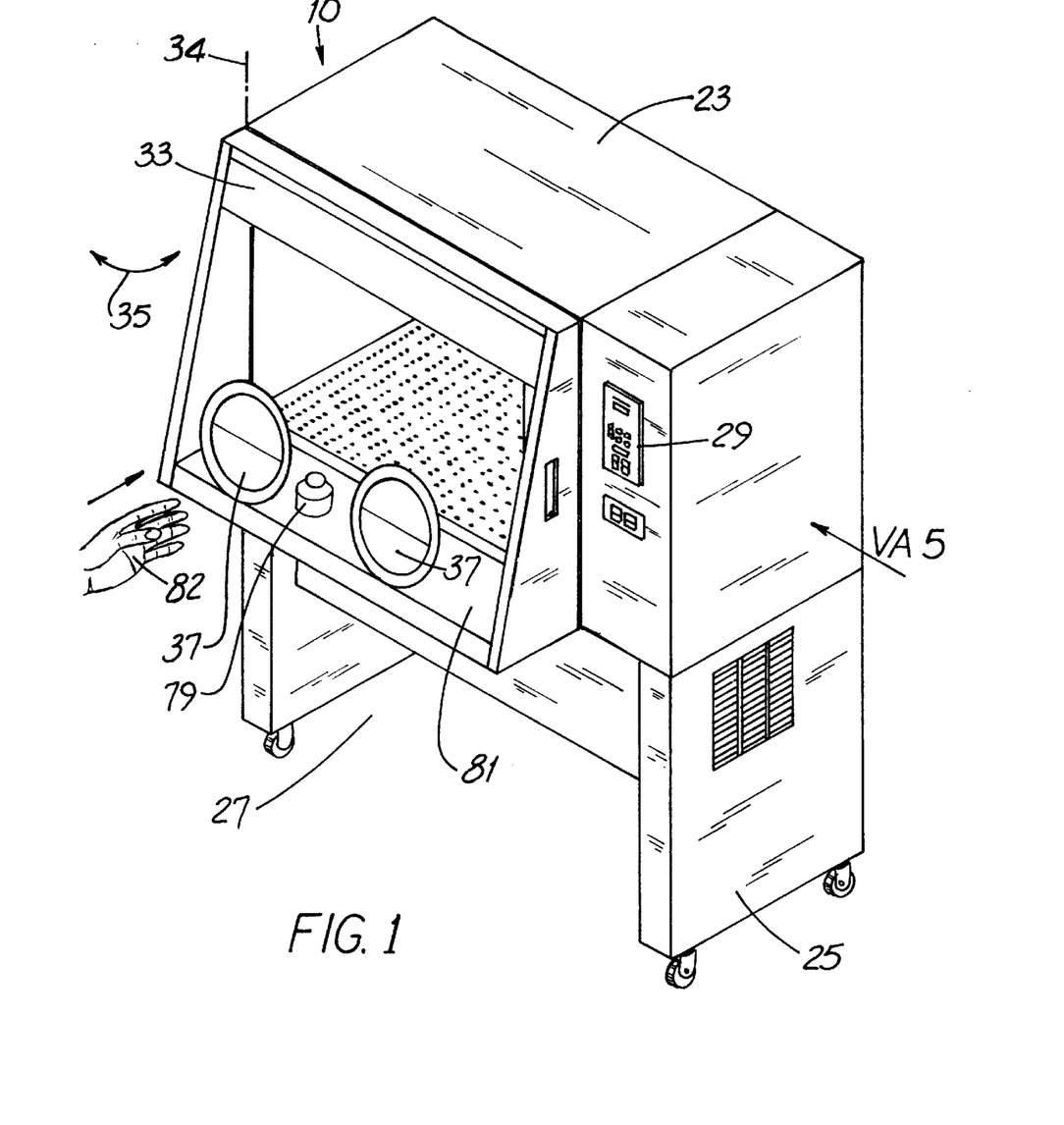
FIG. 1 is a perspective view of the cytogenetic chamber.

Before describing the new cytogenetic chamber 10 of FIG. 1, it will be helpful to have an understanding of the effect of drying time upon metaphase spreading. During drying as shown in FIG. 2, the surface tension of the fixative 12 makes the cell 11 thinner from top to bottom and wider from side to side. (The arrows 14 symbolize the lapse of time.) The cell 11 continues to get thinner and wider as the fixative 12 evaporates.

Figures 2A, 2B:
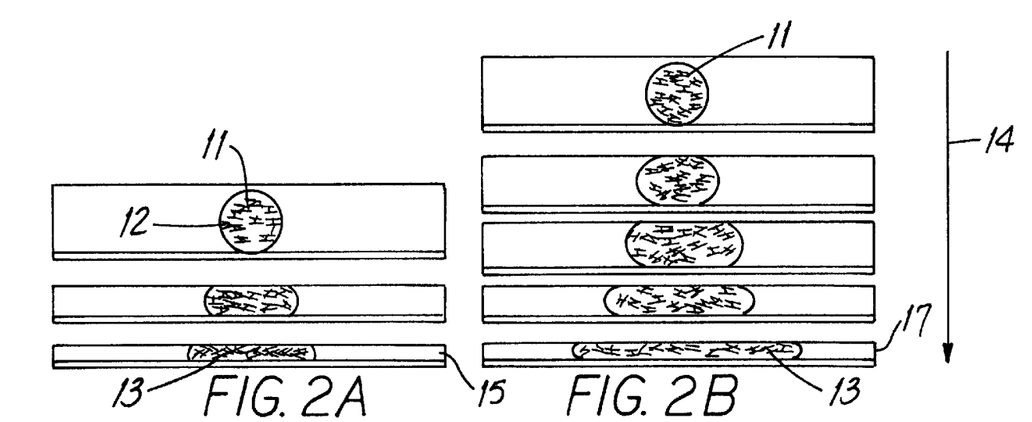
FIGS. 2A–2D show the result of cell fixative drying under various conditions. The top-to-bottom views of each of FIGS. 2A–2D show time-sequence drying.

FIG. 2A shows metaphases 13 that dry too rapidly. As shown in the view 15, such metaphases 13 are often "tight"

and have many overlapping chromosomes. Metaphases 13 dried at the optimum rate as shown in the view 17 of FIG. 2B have few overlaps and are not broken. The chromosomes of such metaphases 13 may thereby be more readily analyzed by microscope to, for example, detect possible genetic defects. Drying time is in the range of 70–90 seconds.

Figure 2C:
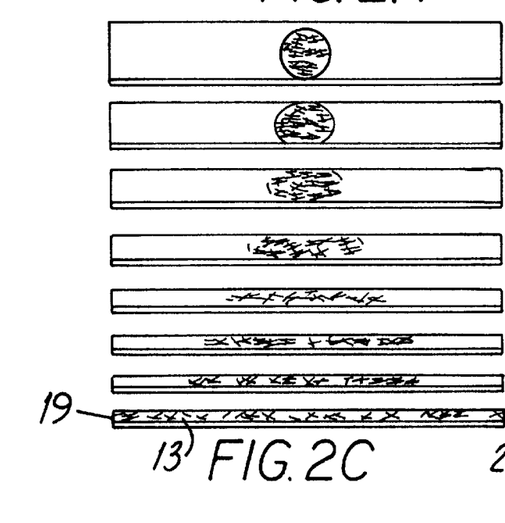
Figure 2D:
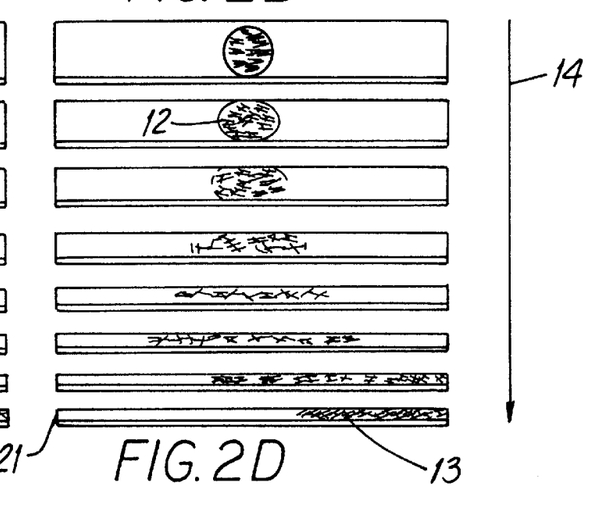

The views 19, 21 of FIGS. 2C and 2D, respectively, show metaphases 13 that dry too slowly. The view 19 shows how such metaphases 13 are characterized by broken metaphases 13 while the view 21 shows how such metaphases 13 are characterized by tight "rolled" metaphases 13. Metaphase drying in the new chamber 10 yields a higher percentage of metaphases 13 like those shown in view 17 than has heretofore been possible.

Referring now to FIGS. 1, 3, 4 and 5 the new chamber 10 has an enclosure 23 in which drying of fixative-treated metaphase and interphase cells occurs. Such enclosure 23 is supported atop a pedestal structure 25, the configuration of which affords "leg room" in the region 27 for a seated person using the chamber 10. In an optional embodiment shown in FIG. 5, the chamber 10a has a similar region 27 away from the viewer of FIG. 1 so that the chamber 10a might be used by two persons simultaneously. Chamber controls 29 are mounted along the edge.

A drying cavity 31 is in the enclosure 23 and the chamber 10 has a laterally-swinging cavity access door 33 mounted with respect to such enclosure 23. The door 33 is hinged along the vertical axis 34 and as symbolized by the arrow 35, such door 33 is movable between open and closed positions and includes at least one (and preferably two) hand-insertion ports 37.

Figure 4:
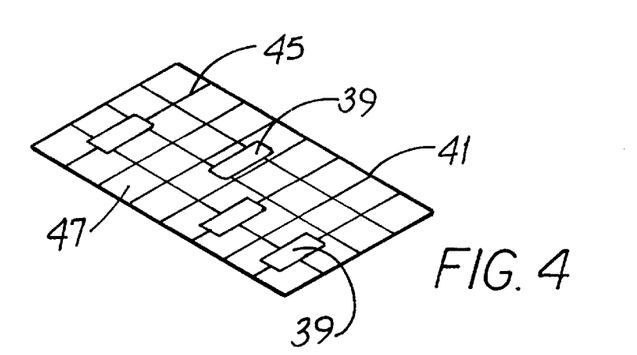
FIG. 4 is a perspective view of an exemplary chamber shelf shown with slides supported thereon for fixative drying.

A fixative-treated cell 11 is prepared on a slide in situ or non in situ and the slide 39 is placed on a rack-like shelf 41 in the cavity drying area 43 (generally bounded by the dashed line 44) for fixative drying. The shelf 41 resembles an oven grate in that such shelf 41 has a number of support strands 45 defining openings 47 therebetween. In plan view, the aggregate area of the support strands 45 is substantially less (perhaps 90–95% less) than the aggregate area of the openings 47.

Figure 3:
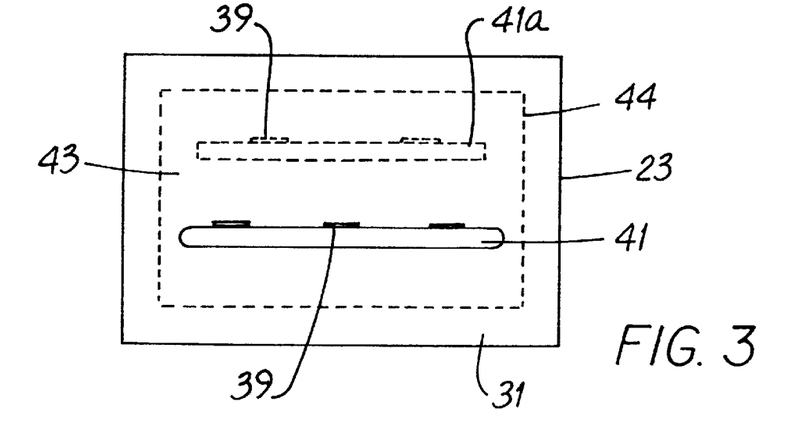
FIG. 3 is a front elevation view of the chamber enclosure. A single shelf is shown in solid outline and a second shelf and the cavity drying area are shown in dashed outline.

As shown in FIG. 3, a second shelf 41a (and even additional shelves 41) may be used in the chamber 10. With plural shelves 41, it is preferred that slides 39 be arranged on such shelves 41 so that no two slides 39 are in vertical registry with one another.

Figure 6:
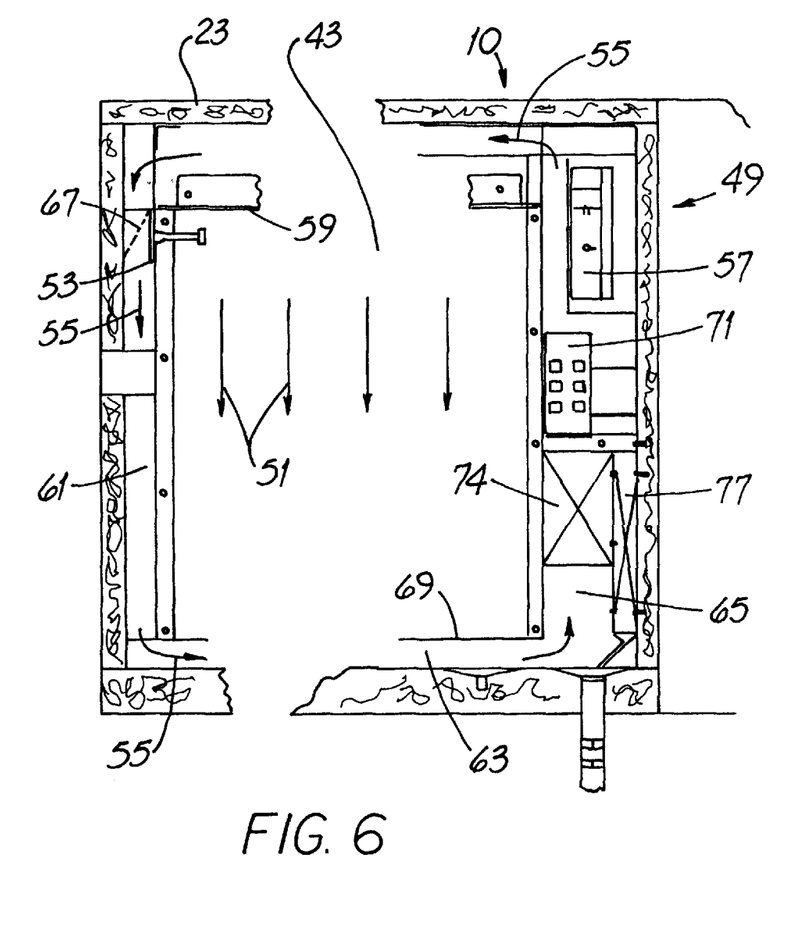
FIG. 6 is a cutaway front elevation view of the chamber showing internal features. Parts are broken away.
Figure 7:
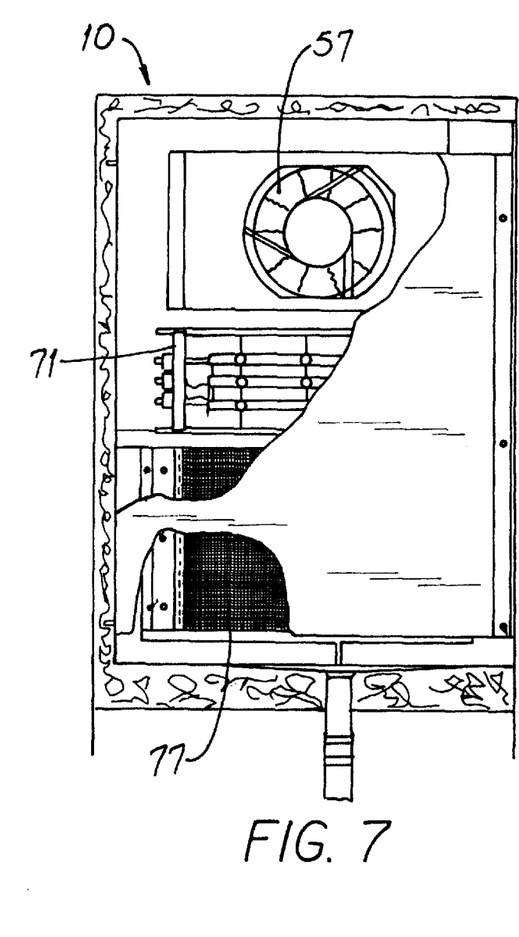

As shown in FIGS. 6 and 7, the chamber has an air-moving system 49 which provides laminar air flow (symbolized by the arrows 51) through the cavity 31 and its drying area 43. In an optional arrangement, the chamber 10 includes an adjustable bypass valve 53 so that the velocity and volume of air flowing through the drying area 43 per unit of time, i.e., the air flow rate, may (within limits) be selected.

With the valve 53 in the open or bypass position shown in FIG. 6, most of the air flows as indicated by the arrows 55 from the fan 57 across the top of the multi-apertured air discharge plenum 59, along the side bypass path 61, along the bottom bypass path 63 and up the return path 65 to the fan inlet. (It is to be appreciated that since each of the plena 59, 69 has holes in it, placing the valve 53 in the bypass position reduces air flow through the drying area 43 but does not entirely eliminate such flow.)

With the valve 53 closed as represented by the dashed line 67 to occlude the side bypass path 61, air flows across the top of the air discharge plenum 59, with a higher proportion of such air flowing downward through the plenum 59 and the drying area 43, through the return plenum 69, along the bottom bypass path 63 and up the return path 65. Of course, setting the valve 53 at some intermediate position causes a smaller or larger proportion to flow through the drying area 43, depending upon whether the valve 53 is more open or more closed.

Figure 8:
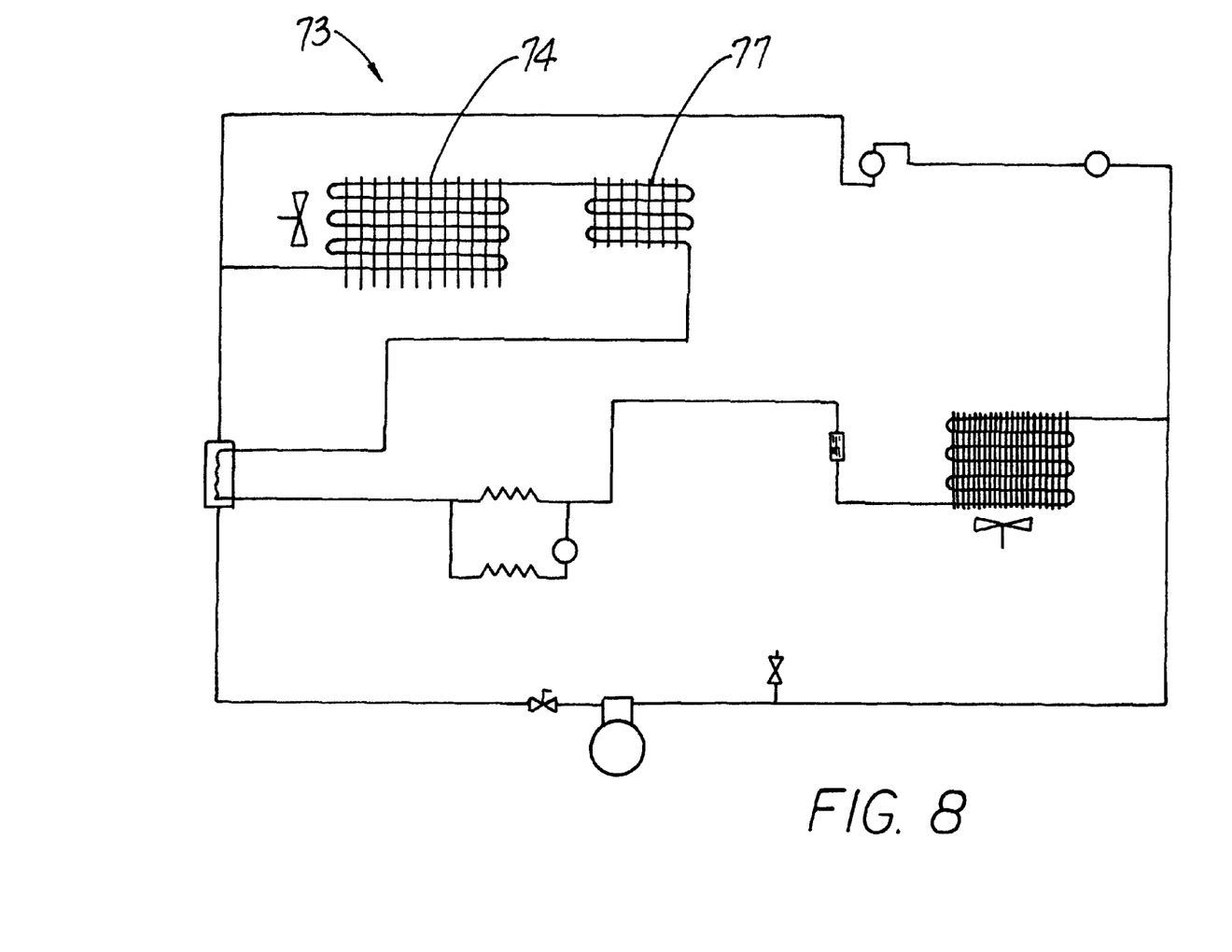
FIG. 8 is a scheematic diagram of the chamber refrigeration system.
Figure 9:
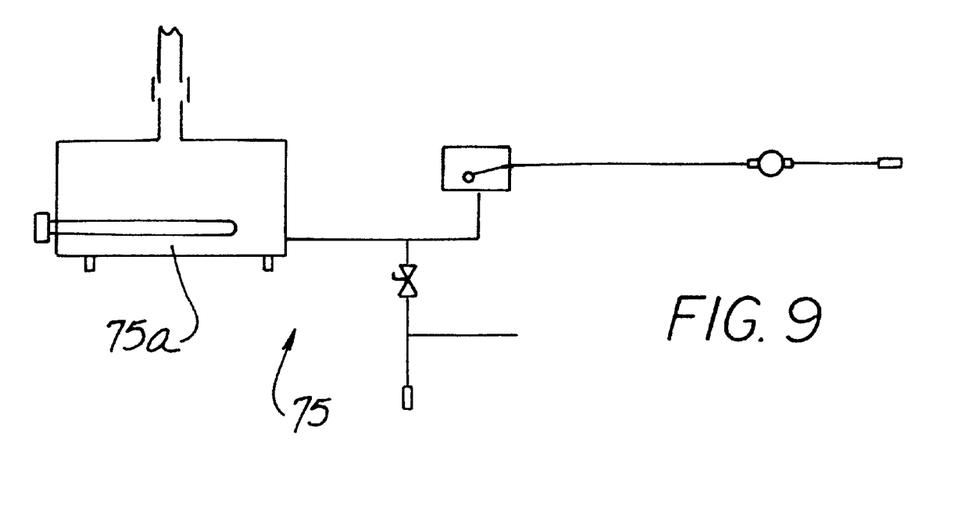
FIG. 9 is a schematic diagram of the chamber steam generating system.

Referring also to FIGS. 8 and 9, a highly-preferred chamber 10 is configured so that both the temperature and the humidity of the air flowing through the drying area 43 can be regulated within rather narrow limits. To that end, the chamber 10 has a heater 71, a refrigeration system 73 and a steam-generating system 75 mounted with respect to the enclosure 23. The evaporator coil 74 and the dehumidifying coil 77 of the system 73 are below the fan 57. The steam generating system 75 has a steam generator 75a for increasing humidity in the cavity 31.

Referring again to FIG. 1, it is advantageous to be able to prepare slides 39 inside the chamber cavity 31 and to maintain containers 79 of liquids use in such preparation generally at the temperature of the air in the cavity 31. The new chamber 10 also has a tray 81 in the enclosure 23 for holding such containers 79. The preferred chamber configuration permits reaching through a hand-insertion port 37, preparing a fixative-treated cell 11 on a slide 39, placing the slide 39 on a chamber shelf 41 and drying the fixative, all while retaining the door 33 in the closed position.

Figure 5:
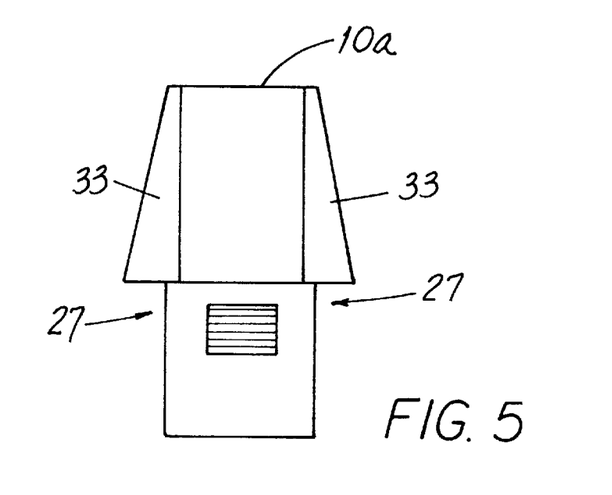
FIG. 5 is an end elevation view of an optional two-door embodiment of the chamber taken generally along the viewing axis VA5 of FIG. 1.

In another, optional, configuration shown in FIG. 5, the chamber 10 may be "double-sided." That is, the chamber 10 may have two access doors 33, one each at the front and rear of the chamber 10. Each door 33 has at least one hand-insertion port 37 so that the chamber 10 may be used simultaneously by two persons.

With a fixative-treated slide-mounted cell 11 in the chamber drying area 43, air flows through the entirety of the drying area 43 at a substantially uniform flow rate and in substantially the same direction, e.g., vertically downward. Preferably, the temperature of the air flowing through the drying area 43 (and impinging on the fixative 12) is substantially uniform throughout such area 43 and, most preferably, the relative humidity of the air flowing through the drying area 43 is also substantially uniform throughout such area 43. The fixative 12 dries at substantially the same drying rate, irrespective of the location of the slide 39 in the drying area 43.

Preferred velocity of air flowing through the drying area is not in excess of about 50 feet (about 152 cm.) per minute and, most preferably, not in excess of about 25 feet (about 76 cm.) per minute. Preferred air temperature is between 15° C. (59° F.) and 35° C. (95° F.) and preferred relative humidity is between 30% and 75%.

(Optimum metaphase areas in the range of 2,100 to 4,500 squared microns—and, most preferably, in the range of 2,500 to 4,500 squared microns—can be achieved at various combinations of relative humidity and temperature. However, it has been found that for amniocytes, 55% rh at 20° C. (68° F.) and for lymphocytes 60% rh at 20° C. often provides the best opportunity—30% or so—to obtain optimum metaphase areas. However, in practice, each specimen has optimum temperature and rh "setpoints." Most often, setpoints of about 25° C. and 50% rh work best. For some patients, chromosome spreading is best at different setpoints of rh and temperature. Therefore, this invention allows the user to optimize the best temperature and humidity settings for a particular specimen.)

A new method for drying a fixative-treated cell 11 supported on a slide 39 includes the steps of providing a cytogenetic chamber 10 with, optionally, a bypass valve 53 which may be adjusted to select the volume of air flowing through the drying area 43 per unit time.

While retaining the door 33 in the closed position, a fixative 12 is applied to the cell 11 (either per se or by mixing fixative 12 with cells 11), the slide 39 supporting the fixative-treated cell 11 is placed on a chamber shelf 41 and the fixative 12 is dried. The applying step includes extending a hand through a hand-insertion port 37 prior to applying the fixative 12 and, most advantageously (at least for convenience), the container 79 holding fixative 12 or a mixture of fixative 12 and cells 11 is available on the tray 81 described above.

The placing step includes grasping the slide 39 with the hand 82 extended through the port 37 and placing the slide 39 at any location within the cubage of the drying area 43. The drying step includes flowing air through the drying area 43 at a substantially uniform flow rate and, preferably, in a substantially uniform direction.

Figure 10:
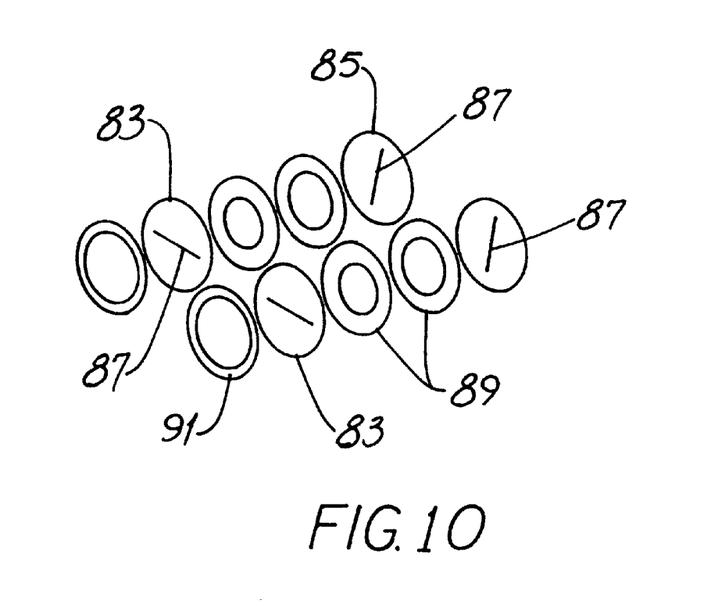
FIG. 10 is an exploded perspective view showing the component parts of a hand-insertion port.

Referring to FIG. 10, in a specific configuration, the hand-insertion port 37 includes two panels 83, 85, each having a straight slit 87 across it. With such configuration, the extending step includes extending the hand sequentially through the panel slits 87.

The panels 83, 85 are spaced apart by two rings 89 and are compressively secured in position by a squash plate 91. The panels 83, 85 are arranged so that the slits 87 are at an angle to one another, preferably an angle other than 0°. In a highly preferred arrangment, such angle is about 90°.

While the principles of the invention have been shown and described in connection with specific embodiments, it is to be understood clearly that such embodiments are by way of example and are not limiting.

What is claimed:

1. In combination, a cytogenetic chamber and a slide supporting a fixative-treated cell, comprising:
   a single drying cavity within said cytogenetic chamber for drying a fixative of said fixative-treated cell, wherein an air temperature of said drying cavity and a humidity of said drying cavity are substantially uniform throughout said drying cavity;
   a horizontal shelf in said drying cavity upon which said slide supporting said fixative-treated cell rests; and
   structure for providing vertical laminar air flow through an entirety of said drying cavity at a substantially uniform flow rate, whereby said fixative dries at substantially a same drying rate, irrespective of a location of said slide in said drying cavity.

2. The combination of claim 1, wherein said air flows through said entirety of said drying area in substantially a same direction.

3. The combination of claim 2, wherein said air flows through said drying area at a velocity not in excess of about 50 feet per minute.

4. The combination of claim 1, wherein a temperature of said air which flows through said drying area is substantially uniform.

5. The combination of claim 4, wherein temperature is between 15° C. and 35° C.

6. The combination of claim 1, wherein a relative humidity of said air which flows through said drying area is substantially uniform.

7. The combination of claim 6, wherein said relative humidity is between 30% and 75%.

8. The combination of claim 1, wherein said cytogenetic chamber includes an adjustable bypass valve, whereby a volume of said air which flows through said drying area may be selected.

9. In combination, a cytogenetic chamber and a slide supporting a fixative-treated cell, comprising:
   a single drying cavity within said cytogenetic chamber for drying a fixative of said fixative-treated cell, wherein an air temperature of said drying cavity and a humidity of said drying cavity are substantially uniform throughout said drying cavity;
   a horizontal shelf in said drying cavity upon which said slide supporting said fixative-treated cell rests;
   structure for providing vertical laminar air flow through an entirety of said drying cavity in substantially a same direction, whereby said vertical laminar air flow impinges on said fixative in substantially a same direction, irrespective of a location of said slide in said drying cavity.

10. The combination of claim 9, wherein a temperature of said air which flows through said drying area is substantially uniform.

11. The combination of claim 9, wherein a relative humidity of said air which flows through said drying area is substantially uniform.

12. The combination of claim 9, wherein said cytogenetic chamber includes an adjustable bypass valve whereby a volume of said air which flows through said drying area may be selected.

13. A cytogenetic chamber comprising:
   a chamber enclosure;
   a single drying cavity within said chamber enclosure, wherein said drying cavity is defined by fixed walls and a hinged door
   and said hinged door is mounted with respect to said chamber enclosure so as to be movable between open and closed positions;
   structure for providing humidified air flowing through said drying cavity; and
   a hand-insertion port through said door, whereby a fixative-treated cell may be slide-mounted on a slide within said chamber enclosure and a fixative of said fixative-treated cell may be dried in said drying cavity.

14. The chamber of claim 13, further comprising a refrigeration system mounted with respect to said chamber enclosure for controlling a temperature of air in said drying cavity.

15. The chamber of claim 14, further comprising a steam generator for controlling a relative humidity of said air in said drying cavity.

16. The chamber of claim 13, further comprising a tray in said chamber enclosure for holding containers used in preparing said fixative-treated cell.

17. The chamber of claim 13, further comprising an air-moving system, wherein:
   said drying cavity includes a rack for supporting said slide upon which said fixative-treated cell is placed; and
   said air-moving system provides laminar air flow through said drying cavity.

18. The chamber of claim 13, wherein said door is a first door, said hand-insertion port is a first port, and said cytogenetic chamber includes a second door mounted with respect to said chamber enclosure, said second door including a second hand-insertion port, whereby said cytogenetic chamber may be used simultaneously by two persons.

* * * * *